United States Patent [19]
Longo et al.

[11] Patent Number: 5,312,746
[45] Date of Patent: May 17, 1994

[54] CLONING AND EXPRESSING RESTRICTION ENDONUCLEASES AND MODIFICATION METHYLASES FROM CARYOPHANON

[75] Inventors: Mary C. Longo, Germantown; Michael D. Smith, Rockville; Deb K. Chatterjee, North Potomac, all of Md.

[73] Assignee: Life Technologies, Inc., Gaithersburg, Md.

[21] Appl. No.: 2,032

[22] Filed: Jan. 8, 1993

[51] Int. Cl.$^5$ .......................... C12N 9/10; C12N 9/22; C12N 1/21
[52] U.S. Cl. ................... 435/193; 435/199; 435/252.33; 435/320.1
[58] Field of Search ............... 435/193, 199, 252.33, 435/320.1

[56] References Cited

U.S. PATENT DOCUMENTS

| | | | |
|---|---|---|---|
| 4,983,542 | 1/1991 | Van Cott et al. | 435/172.3 |
| 4,996,151 | 2/1991 | Brooks et al. | 435/172.3 |
| 5,002,882 | 3/1991 | Lunnen et al. | 435/172.3 |
| 5,082,784 | 1/1992 | Chatterjee et al. | 435/252.3 |
| 5,147,800 | 9/1992 | Hammond et al. | 435/252.3 |
| 5,179,015 | 1/1993 | Wilson et al. | 435/172.3 |
| 5,200,333 | 4/1993 | Wilson | 435/172.3 |

FOREIGN PATENT DOCUMENTS 0193413 9/1986 European Pat. Off.
WO91/14771 10/1991 PCT Int'l Appl.

OTHER PUBLICATIONS

Brooks et al., Cloning the *Bam*HI restriction modification system *Nucleic Acids Research* 17(3):979–997 (1989).
Card et al., Cloning and characterization of the *Hpa*II methylase gene, *Nucleic Acids Research* 18(6):1377–1383 (1990).
Darzins et al., Cloning of Genes Controlling Alginate Biosynthesis from a Mucoid Cystic Fibrosis Isolate of *Pseudomonas aeruginosa*, *Journal of Bacteriology* 159(1):9–18 (1984).
Hammond et al., Cloning *Kpn*I restriction–modification system in *Escherichia coli*, *Gene* 97:97–102 (1991).
Howard et al., Cloning the *Dde*I restriction–modification system using a two-step method, *Nucleic Acids Research* 14(20):7939–7951 (1986).
Janulaitis et al., Cloning of the modification methylase gene of *Bacillus centrosporus* in *Escherichia coli*, *Gene* 20:197–204 (1982).
Kiss et al., Molecular cloning and expression in *Escherichia coli* of two modification methylase genes of *Bacillus subtilis*, *Gene* 21:111–119 (1983).
Mann et al., Cloning of Restriction and Modification Genes in *E. coli*: The *Hha*II System From *Haemophilus haemolyticus*, *Gene* 3:97–112 (1978).
New England Biolabs Catalogue, pp. 25 and 52 (1992).
Piekarowicz et al., A new method for the rapid identification of genes encoding restriction and modification enzymes, *Nucleic Acids Research* 19(8):1831–1835 (1991).
Roberts, R. J., Restriction enzymes and their isoschizomers, *Nucleic Acids Research* 17(Suppl):r347–r387 (1989).

(List continued on next page.)

Primary Examiner—Charles L. Patterson, Jr.
Attorney, Agent, or Firm—Sterne, Kessler, Goldstein & Fox

[57] ABSTRACT

The present invention is directed to recombinant hosts which contain and express the ClaI Type-II restriction endonuclease and/or modification methylase genes. The present invention is also directed to vectors or DNA molecules which contain these gene, and to methods of producing the enzymes. One source of these enzyme is *Caryophanon latum*, although other microorganisms may be used to isolate the restriction endonuclease isoschizomers and modification methylase isoschizomers of the invention.

44 Claims, 2 Drawing Sheets

OTHER PUBLICATIONS

Stratagene Catalog p. 98 (1989).

Szomolanyi et al., Cloning the modification methylase gene of *Bacillus sphaericus* R in *Escherichia coli*, *Gene* 10:219–225 (1980).

Van Cott et al., Cloning the *Fnu*DI, *Nae*I, *Nco*I and *Xba*I restriction-modification systems, *Gene* 74:55–59 (1988).

Vieira et al., The pUC plasmids, an M13mp7-derived system for insertion mutagenesis and sequencing with synthetic universal primers, *Gene* 19:259–268 (1982).

Walder et al., Cloning of the *Msp*I Modification Enzyme, The Site of Modification and Its Effects on Cleavage by *Msp*I and *Hpa*II, *The Journal of Biological Chemistry* 258(2):1235–1241 (1983).

Wilson, G. G., Organization of restriction-modification systems, *Nucleic Acids Research* 19(10):2539–2566 (1991).

Wilson, G. G. Type II restriction-modification systems, *TIG* 4(11):314–318 (1988).

Mayer, H. et al. (1981) Nuc. Acids Res. 9(19), 4833–4845.

McClelland, M., et al. (1981) Nuc. Acids Res. 9(24)6795–6804.

Lunnen, K. P. et al. (1988) Gene 74, 25–32.

Wilson, G. G (1988) Gene 74, 281–289.

CLONING AND EXPRESSING RESTRICTION ENDONUCLEASES AND MODIFICATION METHYLASES FROM CARYOPHANON

FIELD OF THE INVENTION

The present invention is in the field of genetic engineering and molecular biology. This invention is directed to recombinant hosts expressing restriction endonucleases and modification methylases from the genus Caryophanon. This invention is specifically directed to the recombinant hosts and vectors which contain the genes coding for the restriction endonuclease ClaI and its corresponding methylase. This invention is also directed to the cloned restriction endonuclease and modification methylase isoschizomers of these enzymes.

BACKGROUND OF THE INVENTION

Restriction endonucleases are a class of enzymes that occur naturally in prokaryotic and eukaryotic organisms. When restriction endonucleases are purified away from other contaminating cellular components, the enzymes can be used in the laboratory to cleave DNA molecules in a specific and predictable manner. Thus, restriction endonucleases have proved to be indispensable tools in modern genetic research.

Restriction endonucleases cleave DNA by recognizing and binding to particular sequences of nucleotides (the "recognition sequence") along the DNA molecule. The enzymes cleave both strands of the DNA molecule within, or to one side of, this recognition sequence.

Different restriction endonucleases have affinity for different recognition sequences. About 100 kinds of different endonucleases have so far been isolated from many microorganisms, each being identified by the specific base sequence it recognizes and by the cleavage pattern it exhibits. In addition, a number of restriction endonucleases, called restriction endonuclease isoschizomers, have been isolated from different microorganisms which in fact recognize the same recognition sequence as those restriction endonucleases that have previously been identified. These isoschizomers, however, may or may not cleave the same phosphodiester bond as the previously identified endonuclease.

Modification methylases are complementary to their corresponding restriction endonucleases in that they recognize and bind to the same recognition sequence. However, in contrast to restriction endonucleases, the modification methylases chemically modify certain nucleotides within the recognition sequence by the addition of a methyl group. Following this methylation, the recognition sequence is no longer bound or cleaved by the restriction endonuclease. Thus, in nature, methylases serve a protective function, i.e., to protect the DNA of an organism which produces its corresponding restriction enzyme.

Restriction enzymes and modification methylases can be purified from the host organism by growing large amounts of cells, lysing the cell walls, and purifying the specific enzyme away from the other host proteins by extensive column chromatography. However, the amount of restriction enzyme relative to that of the other host proteins is usually quite small. Thus, the purification of large quantities of restriction enzymes or methylases by this method is labor intensive, inefficient, and uneconomical.

An alternative method for producing large quantities of restriction and modification enzymes is to clone the genes encoding the desired enzymes and overexpress the enzymes in a well studied organism, such as *Escherichia coli* (*E. coli*). In this way, the amount of restriction and modification enzymes, relative to that of the host proteins, may be increased substantially. The first cloning of a DNA endonuclease gene was described by Mann et al. *Gene* 3:97-112 (1978). Since then more than seventy DNA methylase and restriction endonucleases have been cloned. Thus far, the majority of the restriction endonuclease genes are closely linked to their corresponding methylase genes.

Restriction-modification systems can be cloned by several methods. A number of endonuclease and methylase genes have been cloned from endogenous plasmids: EcoRII (Kosykh et al., *Mol. Gen. Genet.* 178:717-718 (1980)), EcoRI (Newman et al., *J. Biol. Chem.* 256:2131-2139 (1981)), Greene et al., *J. Biol. Chem.* 256:2143-2153 (1981)), EcoRV (Bougueleret et al., *Nucl. Acids Res.* 12:3659-3676 (1984)), PvuII (Blumenthal et al., *J. Bacteriol.* 164:501-509 (1985)), KpnI (Hammond et al., Gene 97: 97-102 (1990)), and PaeR71 (Gingeras et al., *Proc. Natl. Acad. Sci.* USA 80:402-406 (1983)). An alternative method of cloning is the phage restriction method in which bacterial cells carrying cloned restriction and modification genes survive phage infection (Mann et al., supra; Walder et al., *Proc. Natl. Acad. Sci. U.S.A.* 78:1503-1507 (1981); Rodicio et al., *Mol. Gen. Genet.* 213:346-353 (1988)). Another procedure is based upon methylation protection and has been suggested by Mann et al., supra, and Szomolanyi et al., *Gene* 10:219-225 (1980). This latter scheme involves digestion of a plasmid library with the restriction enzyme to be cloned. Only those plasmids with DNA sequences modified by the corresponding methylase will be resistant to digestion and will produce transformants in a suitable host. This selection method has been used to clone endonuclease and methylase genes together as well as to clone methylase genes alone (Szomolanyi et al., supra; Janulaitis et al., *Gene* 20:197-204 (1982); Walder et al., *J. Biol. Chem.* 258:1235-1241 (1983); Kiss et al., *Gene* 21:111-119 (1983); Wilson, *Gene* 74:281-289 (1988)). However, this technique sometimes yields only the methylase gene, even though the endonuclease and modifying genes are closely linked.

A multi-step approach has been required to clone certain restriction-modification systems in E. coli, including DdeI (Howard et al., *Nucl. Acids Res.* 14:7939-7950 (1989)), BamHI (Brooks et al., *Nucl. Acids Res.* 17:979-997 (1989)), KpnI (Hammond et al., supra) and ClaI (disclosed herein). In each case, protection of the host with methylase expressed on a plasmid was necessary to stabilize a compatible vector containing the functional endonuclease gene. Wilson, supra, has proposed a model to explain why certain restriction-modification systems must be cloned utilizing a protected host. This model proposes that in order to establish a plasmid carrying a restriction-modification system, methylase protection must occur at a rate that is greater than the rate of endonuclease digestion. Otherwise, restriction enzymes would cleave unmethylated plasmid and/or genomic DNA and degrade the plasmid and/or kill the host. Although this model is a plausible explanation of plasmid establishment, it has yet to be determined whether continued independent expression of methylase from a separate plasmid is necessary to maintain the plasmid carrying the restriction-modification system during cell growth and replication.

SUMMARY OF THE INVENTION

The present invention is directed to recombinant hosts which contain and express the Type-II restriction endonuclease and modification methylase genes of the present invention. The restriction endonuclease and modification methylase of the invention recognize the palindromic sequence:

5'ATCGAT3'

3'TAGCTA5'.

The isoschizomers of this class of restriction endonucleases are exemplified by ClaI and cleave the sequence between the deoxythymidine (T) and deoxycytidine (C) residues from the 5' end, producing a two-base 5' extension:

5'AT ↓ CG AT3'

3'TA GC ↑ TA5'.

The modification methylase enzymes of the present invention chemically modify the recognition sequence, thus rendering the sequence resistant to cleavage by the complementary restriction enzyme.

This invention is further directed to vectors comprising a Caryophanon gene coding for the restriction endonuclease and/or modification methylase.

This invention is further directed to processes for obtaining these enzymes and the use thereof. According to the process of this invention, the restriction endonuclease and/or modification methylase is produced by culturing a recombinant host comprising a Caryophanon gene for the restriction endonuclease and/or modification methylase and isolating enzymes from the recombinant host.

In particular, the present invention is concerned with genes coding for restriction endonuclease, ClaI, and its corresponding modification methylase.

DEFINITIONS

Figure 1:
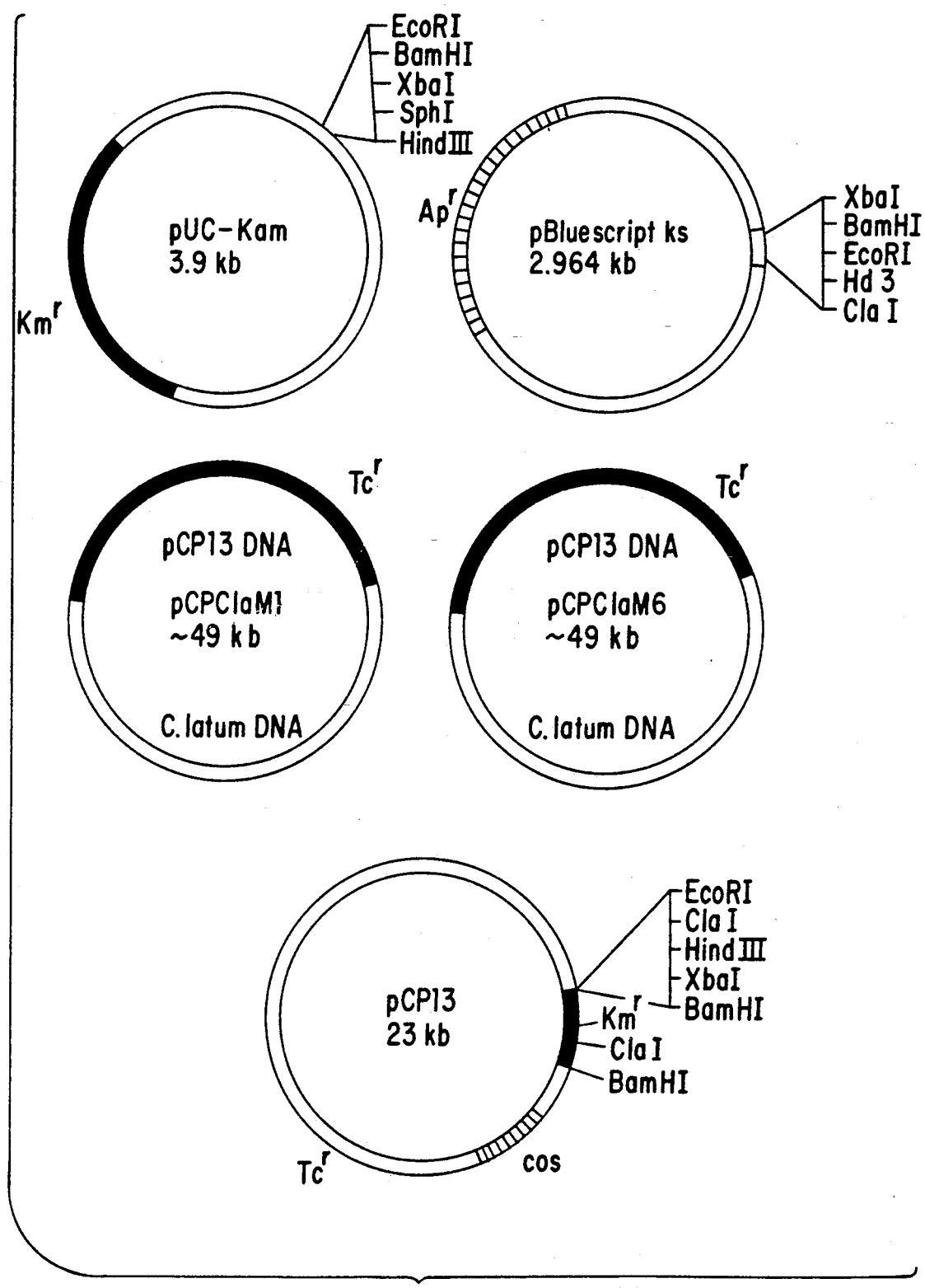
FIG. 1 shows schematic maps of the vectors pCP13, pBluescript KS, pUC-Kam, pCPClaIM1, and pCPClaIM6. The figure also shows the location of the plasmid genes which confer resistance to the antibiotics kanamycin (Km$^r$), ampicillin (Ap$^r$), and tetracycline (Tc$^r$), as well as the location of the cohesive ends (COS) in pCP13. The size of each vector is indicated in kilobases (kb).

In the description that follows, a number of terms used in recombinant DNA technology are utilized extensively. In order to provide a clear and consistent understanding of the specification and claims, including the scope to be given such terms, the following definitions are provided.

Cloning vector. A plasmid or phage DNA or other DNA sequence which is able to replicate autonomously in a host cell, and which is characterized by one or a small number of restriction endonuclease recognition sites at which such DNA sequences may be cut in a determinable fashion without loss of an essential biological function of the vector, and into which a DNA fragment may be spliced in order to bring about its replication and cloning. The cloning vector may further contain a marker suitable for use in the identification of cells transformed with the cloning vector. Markers, for example, provide tetracycline resistance or ampicillin resistance.

Expression vector. A vector similar to a cloning vector but which is capable of enhancing the expression of a gene which has been cloned into it, after transformation into a host. The cloned gene is usually placed under the control of (i.e., operably linked to) certain control sequences such as promoter sequences. Promoter sequences may be either constitutive or inducible.

Substantially pure. As used herein means that the desired purified enzyme is essentially free from contaminating cellular components, said components being associated with the desired enzyme in nature, as evidenced by a single band following polyacrylamide-sodium dodecyl sulfate gel electrophoresis. Contaminating cellular components may include, but are not limited to, phosphatases, exonucleases or other undesirable endonucleases.

Restriction endonuclease isoschizomer. A restriction endonuclease isoschizomer is a term used to designate a group of restriction endonucleases that recognize and bind to the same recognition sequence but are isolated from different microbial sources. Restriction endonuclease isoschizomers may or may not cleave in the exact location as the restriction endonuclease with which it is being compared.

Modification methylase isoschizomer. A modification methylase isoschizomer is a term used to designate a group of modification methylases that recognize the same recognition sequence but are isolated from different microbial sources. Modification methylase isoschizomers may or may not chemically modify the same nucleotides within the recognition sequence as the restriction endonuclease with which it is being compared.

Recognition sequence. Recognition sequences are particular DNA sequences which a restriction endonuclease or a modification methylase recognizes and binds. Recognition sequences are typically four to six (and in some cases, eight) nucleotides in length with a two-fold axis of symmetry.

Recombinant Host. According to the invention, a recombinant host may be any prokaryotic or eukaryotic microorganism which contains the desired cloned genes on an expression vector or cloning vector. This term is also meant to include those microorganisms that have been genetically engineered to contain the desired gene(s) in the chromosome or genome of that organism. The term "recombinant host" is not meant to include the wild type Caryophanon strain which produces ClaI.

Recombinant vector. Any cloning vector or expression vector which contains the desired cloned gene(s).

Host. Any prokaryotic or eukaryotic microorganism that is the recipient of a replicable expression vector or cloning vector. A "host", as the term is used herein, also includes prokaryotic or eukaryotic microorganisms that can be genetically engineered by well known techniques to contain desired gene(s) on its chromosome or genome. For examples of such hosts, see Maniatis et al., *Molecular Cloning: A Laboratory Manual*, Cold Spring Harbor Laboratory, Cold Spring Harbor, N.Y. (1982).

Promoter. A DNA sequence generally described as the 5' region of a gene, located proximal to the start codon. The transcription of an adjacent gene(s) is initiated at the promoter region. If a promoter is an inducible promoter, then the rate of transcription increases in response to an inducing agent. In contrast, the rate of transcription is not regulated by an inducing agent if the promoter is a constitutive promoter.

Gene. A DNA sequence that contains information needed for expressing a polypeptide or protein.

Structural gene. A DNA sequence that is transcribed into messenger RNA (mRNA) that is then translated into a sequence of amino acids characteristic of a specific polypeptide.

Expression. Expression is the process by which a polypeptide is produced from a structural gene. The process involves transcription of the gene into mRNA and the translation of such mRNA into polypeptide(s).

Nomenclature for naming restriction endonucleases are in accord with the proposal of Smith et al., *J. Mol. Biol.* 81: 419–423 (1973). Briefly, the first letter "C" of ClaI designates the genus "Caryophanon" while the lower case letters "la" designate the species "latum." Thus, the original strain found to produce ClaI was designated *Caryophanon latum* ("BRL 240").

DETAILED DESCRIPTION OF THE INVENTION

This invention is directed to recombinant hosts which express the gene coding for the Type-II restriction endonuclease ClaI and to DNA molecules which contain the gene. ClaI recognizes the palindromic sequence 5' ATCGAT3', cleaving between the T and C residues from the 5' end, producing a two-base 5' extension. The double-stranded recognition site of ClaI is thus characterized as follows:

5'AT ↓ CG AT3'

3'TA GC ↑ TA5'

(wherein A represents deoxyadenosine, T represents deoxythymidine, G represents deoxyguanosine, and C represents deoxycytidine).

This present invention is further directed to gene(s) coding for the modification methylase genes which are complementary to the ClaI restriction endonuclease. These methylases chemically modify certain nucleotides with the recognition sequence by the addition of a methyl group, thus making the modified sequence resistant to cleavage by the complementary restriction endonuclease.

Also provided by this invention are recombinant hosts and DNA molecules which contain genes coding for isoschizomers of the restriction endonuclease and modification methylase of the present invention. Methods for producing the enzymes of the invention are also disclosed.

I. Isolation of the Genes Coding for the Restriction Endonuclease and Modification Methylase or Isoschizomers thereof The restriction endonuclease (ClaI) and its corresponding modification methylase may be obtained from any strain of *C. latum*. Genes coding for isoschizomers of these enzymes can be obtained from any genus including, but not limited to, Arthrobacter, Bacillus, Citrobacter, Enterobacter, Escherichia, Flavobacterium, Caryophanon, Klebsiella, Micrococcus, Xanthomonas, Nocardia, Pseudomonas, Salmonella, and Streptomyces. The preferred genus to isolate isoschizomers of the restriction endonuclease of the present invention is Caryophanon.

Any strain of Caryophanon capable of producing restriction endonuclease isoschizomers of ClaI can be used for the purpose of this invention. For example, *Caryophanon tenue* may be used to obtain the genes expressing the restriction endonuclease isoschizomers of ClaI. Restriction endonuclease isoschizomers of ClaI may also be obtained from *Bacillus aneurinolyticus* (BanIII), *Bacillus subtilus* (BstI), Achromobacter species (Asp707I), or Bacillus species (BscI).

The preferred species for obtaining the gene encoding the enzyme of the present invention is *Caryophanon latum* as described in the examples.

II. Cloning and Expressing the Genes Coding for the Restriction Endonuclease and Modification Methylase or Isoschizomers thereof ClaI and ClaI methylase are preferably obtained by isolating the genes coding for the enzymes from *Caryophanon latum* and then cloning and expressing them. It is understood in this invention that genes coding for isoschizomers of the restriction endonucleases and modification methylases of the present invention may be obtained from any microorganism including the genus Caryophanon by using the recombinant techniques described herein.

DNA molecules which code for ClaI and ClaI methylase, or isoschizomers thereof, can be recombined into a cloning vector and introduced into a host cell to enable the expression of the restriction endonuclease or modification methylase by that cell. DNA molecules may be recombined with vector DNA in accordance with conventional techniques, including restriction digestion to provide appropriate termini, filling in of cohesive ends as appropriate, alkaline phosphatase treatment to avoid undesirable joining, and ligation with appropriate ligases.

a. Hosts for Cloning and Expressing

The present invention encompasses the expression of the desired restriction endonuclease and modification methylase in prokaryotic and eukaryotic cells. Eukaryotic and prokaryotic hosts that may be used for cloning and expressing the enzymes of the invention are well known in the art. Vectors which replicate in such host cells are also well known (Maniatis et al., *Molecular Cloning: A Laboratory Manual*, Cold Spring Harbor Laboratory Press, Cold Spring Harbor, N.Y. (1982)).

Preferred prokaryotic hosts include, but are not limited to, bacteria of the genus Escherichia, Bacillus, Streptomyces, Pseudomonas, Salmonella, Serratia, Caryophanon, etc. The most preferred prokaryotic host is *E. coli*. Bacterial hosts of particular interest in the present invention include *E. coli* K12, and DH10B (F−, araD139 Δ (ara, leu) 7697, ΔlacX74, galU, galK, mcrA, Δ(mrr hsd RMS mcrB), rpsL dor, Φ 80 d lacZ ΔM15, endA1, nupG, recA1).

It has been found that *E. coli* has several mechanisms (restriction systems) for identifying foreign DNA and destroying it. This can be a significant problem in cloning experiments, resulting in reduced recovery of the desired sequences. In particular, it has been found that *E. coli* contains restriction systems that degrade DNA when it is methylated, either on cytosine residues or adenine residues. Specifically, the well known methylcytosine-specific systems include mcrA (rglA), and mcrB (rglB) (Revel et al., *Virology* 31: 688-701 (1967); Raleigh et al., *Proc. Natl. Acad. Sci.* USA 83: 9070-9074 (1986)). The methyladenine-specific restriction system has been designated mrr (Heitman et al., *J. Bacteriol.* 169: 3243-3250 (1987)). Thus, the preferred host for cloning and expressing the genes encoding for the enzymes of the present invention are hosts in which these types of restriction systems have been inactivated through mutation or loss.

b. Methods for Cloning and Expressing

ClaI and ClaI methylase, or isoschizomers thereof, are preferably obtained by isolating the genes coding for the enzymes and then cloning and expressing them. Four different techniques for isolating and cloning restriction endonucleases and modification methylases have been described in a review by Wilson, *Gene* 74: 281-289 (1988). The four methods reviewed include: (1) subcloning of natural plasmids; (2) selection based on phage restriction; (3) selection based on vector modification involving methylation protection; and (4) multistep isolation.

The methylation protection method for cloning restriction endonuclease genes relies on the proximity of the methylase and restriction enzyme genes to each other and on the expression of both genes in the host cell such as *E. coli*. First, a library is constructed by ligating fragmented genomic DNA from the source organism into a vector. For this library, one chooses a vector having one or, preferably, more recognition sites of the restriction enzyme one wishes to clone. Preferably, vector pCP13 is used to construct the plasmid library (Darzins, A. et al., *J. Bacteriol.* 159: 9-18 (1984)). Generally, library inserts are prepared by only partially digesting the genomic DNA in order to obtain a portion of DNA fragments which contain the intact gene of interest. Second, this library is introduced into and grown in a suitable host such as *E. coli*. Vector DNA that is subsequently isolated from these transformed and grown cells is called the plasmid library. The plasmid library is a mixture of different DNA molecules, having virtually all possible inserts and thus, is representative of most, if not all, DNA sequences contained in the source organism. The vector/insert combinations having a methylase gene will have methylated the recognition sequences within the vector/insert DNA and the host chromosomal DNA if the methylase is expressed in the host used, preferably, *E. coli*.

The isolated plasmid library DNA is then digested with the restriction enzyme. Unmethylated vector/insert combinations are degraded and methylated combinations survive the endonuclease treatment. The endonuclease-treated DNA is then introduced into a fresh host cell. Degraded vector/insert combinations do not become established. Methyl-protected vector/insert combinations, which survived the endonuclease treatment, can establish and maintain themselves in the new *E. coli* host cells, thereby forming clones.

Cell extracts of these clones are then assayed for restriction endonuclease activity in order to identify clones which express the desired restriction enzyme. Thus, genes for a methylase-restriction system can be cloned on a single recombinant DNA molecule, provided that the restriction endonuclease gene is closely linked to the methylase gene.

There are a number of reasons why the above method might not work with a particular endonuclease-methylase system. (1) The two genes (methylase and endonuclease) may not be closely linked. In that case, both genes cannot be on the same DNA fragment insert. (2) The cloned fragment may, by chance, contain only the methylase gene. For example, a closely linked endonuclease gene might be inactivated by being cut by the restriction enzyme that generated the DNA library. Similarly, the methylase and endonuclease genes may have been separated from each other by a cleavage at an intervening restriction site. (3) The level of expression of the endonuclease may be high relative to the expression level of the methylase. In this situation, before the expressed methylase can protect the host DNA, the expressed endonuclease destroys the vector/insert combination as well as degrades the chromosome(s) and may kill the host cell. Alternatively, a deletion(s) resulting in loss of part or all of the endonuclease gene from the vector/insert combination may allow the host to survive. (4) The methylase gene may not be expressed in the new host, leading to lack of protection of DNA from the endonuclease. (5) The endonuclease gene may not be expressed in the new host. In situations (1) and (3), if the endonuclease is expressed in the host, there will be no methylase enzyme activity to protect DNA in the host cell and the attempt to clone the endonuclease would fail.

Surprisingly, the usual methods for cloning restriction system genes were unsuccessful for the ClaI restriction/modification system. Hybridization analyses indicated that the structure of the ClaI methylase gene isolated from *Caryophanon latum* genomic libraries differed from the structure of the ClaI methylase gene in the *C. latum* chromosome. One hypothesis that could explain this unexpected result was that the ClaI endonuclease gene was closely linked to the ClaI methylase gene in the *C. latum* chromosome but that endonuclease gene expression was toxic to the host. In this case, the only clones which would survive would be those in which the link between ClaI and ClaI methylase was disrupted by a rearrangement of the DNA. Thus, an intact clone of the ClaI endonuclease and methylase genes might be obtained if ClaI methylase was present in the recombinant host before introducing the genomic library.

In the present invention, genomic DNA was isolated from a ClaI producing strain of *Caryophanon latum*. Using standard techniques well-known to those in the art, a recombinant DNA library was constructed, the library was introduced into a bacterial host, and DNA insert/vector molecules were isolated from host cells.

A portion of the first DNA library was digested with ClaI and the resulting DNA digest was introduced into fresh host cells. Clones were selected and DNA samples from these clones were screened for resistance to digestion with ClaI. Clones containing DNA resistant to ClaI harbored insert/vector combinations that carried the ClaI methylase. The ClaI methylase gene was then subcloned into a different vector which contained at least one ClaI site and introduced into a bacterial host. The resulting transformants express ClaI methylase but not ClaI endonuclease.

Figure 2:
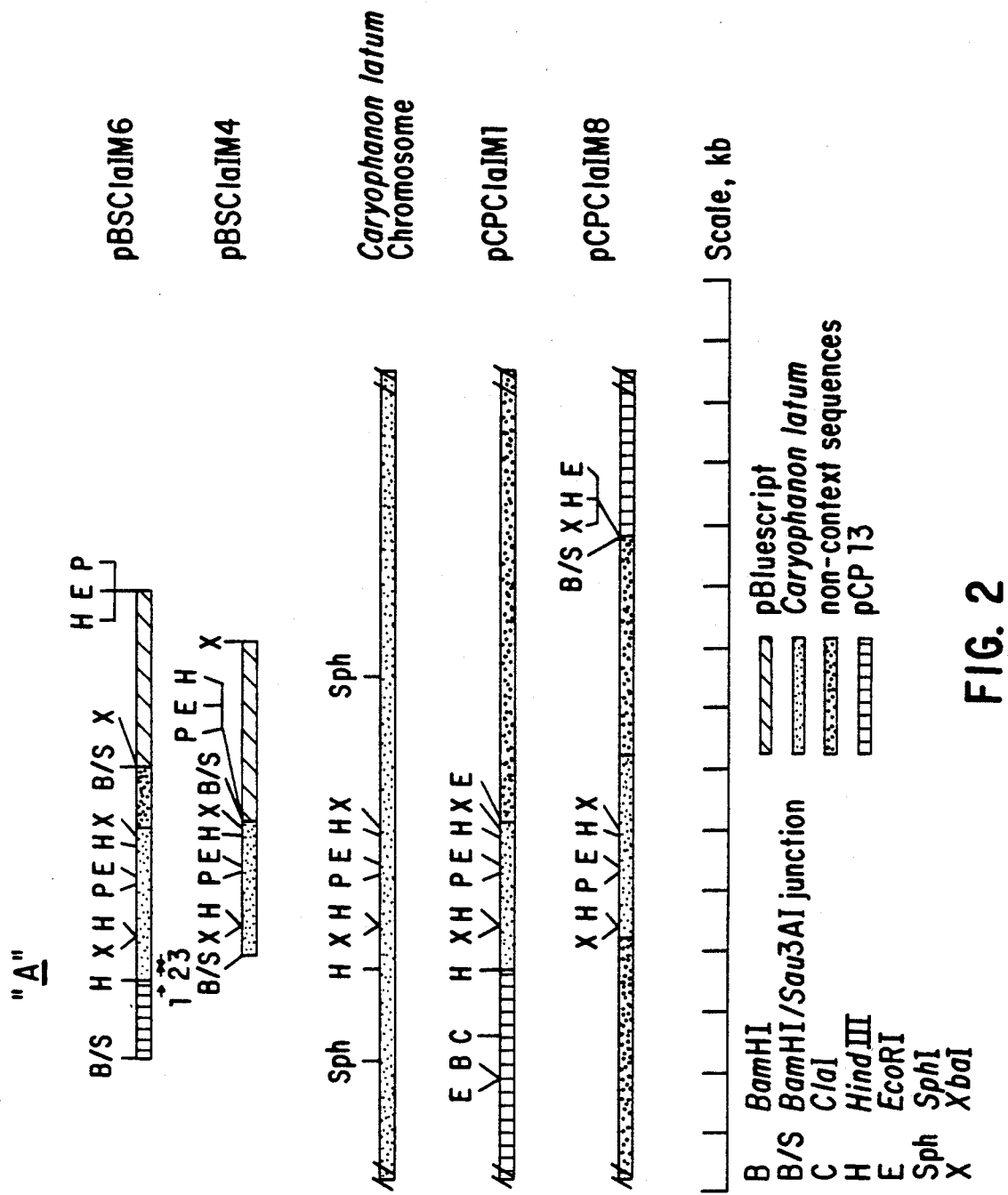
FIG. 2 shows a restriction map of C. latum DNA in the region of the ClaI restriction-modification system and the clones derived from this region. The figure also shows the location of probe "A" DNA sequences. Slashed lines (//) indicate that the DNA molecules are not shown in their entirety and extend beyond the scope of the diagram.

A second genomic library was constructed by introducing *C. latum* genomic DNA into the recombinant host which harbored the ClaI methylase vector. In order to distinguish transformants containing ClaI endonuclease gene sequences from transformants which merely carried the protecting ClaI methylase vector, it was necessary to devise a DNA probe which codes for DNA sequences that are contiguous with, but distinct from, the ClaI methylase gene sequences. For example, oligonucleotide synthesis or polymerase chain reaction technology may be used to produce probes with sequences corresponding to the sequence in the BamHI/-Sau3AI-HindIII fragment of pBSClaIM6 that is not present in pBSClaIM4 (Probe A; FIG. 2). An appropriate DNA probe was used to identify transformants which harbor a plasmid coding for the ClaI endonuclease gene. Cells harboring these clones were then assayed for ClaI endonuclease activity.

Although the steps outlined above are the preferred mode for practicing the present invention, it will be apparent to those skilled in the art that the above-described approach can vary in accordance with techniques known in the art. For example, once the ClaI methylase and/or restriction genes are cloned based on the information disclosed herein, these gene sequences or synthetic oligonucleotides of these sequences may be used in hybridization experiments with genetic material from different organisms to obtain clones which contain these genes. See Maniatis et al., supra. Furthermore, one of ordinary skill in the art, using standard hybridization techniques, can utilize these sequences to isolate genes which code for isoschizomers of the ClaI restriction and modification enzymes by altering the hybridization stringencies.

c. Methods for Enhancing Expression

Once the desired restriction endonuclease and modification genes have been isolated, a number of recombinant DNA strategies exist for enhanced production of the desired protein in eukaryotic or prokaryotic hosts. These strategies, which will be appreciated by those skilled in the art, utilize high copy number cloning vectors, expression vectors, inducible high copy number vectors, etc.

Enhanced production of the restriction endonuclease and modification methylase can be accomplished, for example, by operably linking the desired gene to a strong prokaryotic promoter, although the natural restriction or modification methylase gene promoter may be used. Such well known promoters may be either constitutive or inducible. Examples of constitutive promoters include the int promoter of bacteriophage λ, and the bla promoter of the β-lactamase gene of pBR322, etc. Examples of inducible prokaryotic promoters include the major left and right promoters of bacteriophage λ ($P_L$ and $P_R$), the trp, recA, lacZ, gal, trc, and tac promoters of *E. coli*, the α-amylase (Ulmanen, I., et al., *J. Bacteriol.* 162: 176–182 (1985)), the $\delta^{28}$-specific promoters of *B. subtilis* (Gilman, M. Z., et al., *Gene* 32: 11–20 (1984)), the promoters of the bacteriophages of *Bacillus* (Gryczan, T. J., In: *The Molecular Biology of the Bacilli*, Academic Press, Inc., New York (1982)), and Streptomyces promoters (Ward, J. M., et al., *Mol. Gen. Genet.* 203: 468–478 (1986)). Prokaryotic promoters are reviewed by Glick, B. R., (*J. Ind. Microbiol.* 1: 277–282 (1987)); Cenatiempo, Y. (*Biochimie* 68: 505–516 (1986)); and Gottesman, S. (*Ann. Rev. Genet.* 18: 415–442 (1984)).

In order to enhance the production of the desired restriction endonuclease in a prokaryotic cell, it is important to maintain expression of the corresponding modification methylase gene sufficient to protect the DNA of the recombinant host against cleavage with the cloned restriction endonuclease. Therefore, it may be necessary to enhance the level of methylase expression in conjunction with increased endonuclease activity.

Furthermore, those skilled in the art will recognize that various combinations of maintaining both the modification and restriction genes within the same recombinant host can be constructed. The only requirement, when cloning restriction endonuclease genes, is that the recombinant host contain and express the methylase gene corresponding to the endonuclease gene being cloned.

III. Isolation and Purification of the Restriction Endonuclease and Modification Methylase from Recombinant Hosts The enzymes of this invention, ClaI and ClaI methylase, or isoschizomers thereof, are preferably produced by fermentation of the recombinant host (prokaryotic or eukaryotic) containing and expressing the cloned restriction endonuclease and/or modification methylase genes. The recombinant host, such as *E. coli*, producing the cloned proteins, can be grown and harvested according to techniques well known in the art.

After culturing, the recombinant host cells of this invention can be separated from the culture liquid, for example, by centrifugation. The modification methylase and/or restriction enzymes produced by this host can be extracted and purified by using known protein purification techniques commonly employed for these types of enzymes.

In general, the collected microbial cells are dispersed in a suitable buffer, and then broken down by ultrasonic treatment to allow extraction of the enzyme by the buffer solution. After removal of the residue by ultracentrifugation, desired enzyme can be purified by extraction, ion-exchange chromatography, molecular-sieve chromatography, affinity chromatography, and the like, giving the restriction endonuclease of this invention.

According to the present invention, assays to detect the presence of the restriction endonucleases and modification methylases can be used during the conventional biochemical purification methods to determine the presence of these enzymes.

The restriction endonuclease can be identified on the basis of the cleavage of its recognition sequence. For example, lambda (λ) DNA can be used as a substrate. After digestion with endonuclease, the DNA fragments are separated electrophoretically in agarose gels in the buffer systems conventional for fragment separation and in the presence of ethidium bromide (EtdBr).

Demonstration of modification methylase activity can be, but is not limited to, a two-step identification process. First, substrate DNA (λ DNA) that contains the recognition sequence is incubated with column fractions to be tested for methylase activity. Second, this DNA is then challenged with the corresponding restriction activity to identify those fractions which contain methylase activity. For example, while assaying for ClaI methylase, the DNA samples will be challenged with ClaI. Thus, DNA samples which do not exhibit cleavage with ClaI contain ClaI methylase activity.

The recombinant host (*E. coli* DH10B) containing the genes encoding for ClaI (pCPClaI402) and ClaI methylase (pBSClaIM4) was put on deposit with the Patent Culture Collection, Northern Regional Research Center, USDA, 1815 N. University Street, Peoria, Ill. 61604 USA (NRRL) as deposit No. NRRL B-21039 (deposit date: Dec. 23, 1992).

Having now generally described the invention, the same will be more readily understood through reference to the following Examples which are provided by way of illustration, and are not intended to be limiting of the present invention, unless specified.

EXAMPLE 1

Bacterial Strains and Growth Conditions

*Caryophanon latum* BRL 240 producing the ClaI restriction endonuclease was grown in a 20 liter (l) fermentor at 30° C. to mid-log phase in nutrient media (pH 7.4) consisting of 10 gm/l malt extract ND 201 (Premier Malt Extract), 10 gm/l Hycase S.F. (Sheffield), 5 gm/l sodium acetate, 5 gm/l sodium butyrate, 1 gm/l dibasic potassium phosphate, and 7 gm/l sodium hydroxide. These cells were centrifuged and stored at −70° C. as a cell pellet prior to total genomic DNA isolation.

*E. coli* strains were grown at 37° C. in YET broth (5 gm/l yeast extract, 10 gm/l tryptone, and 5 gm/l NaCl) with antibiotic supplements of 100 mg/l ampicillin; 20 mg/l tetracycline; or 50 mg/l kanamycin, as appropriate. *E. coli* strains DH10B and DH10B/pBSClaIM4 were used for cloning the ClaI genes. DH10B is a recA1−, endA−, Φ 80 d lacZ ΔM15 derivative of MC1061 (Casadaban et al., *J. Mol. Biol.* 138: 179–207 (1980)). Competent and electrocompetent *E. coli* strains were either obtained from Life Technologies, Inc. (LTI; 8717 Grovemont Circle, Gaithersberg, Md. 20884-9980) or made by a protocol described by Hanahan, *J. Mol. Biol.* 166: 557–580 (1983). Electroporation was performed at 2.5 kV in a 0.15 cm gap with a pulse length of about 4 milliseconds.

EXAMPLE 2

Construction of pCP13, pBluescript KS, and pUC-Kam

Since a methylase protection scheme was to be used to clone ClaI restriction and modification genes, it was necessary to use vectors containing ClaI site(s). Plasmid pBluescript KS, containing a single ClaI site, was obtained from Stratagene (Stratagene Cloning Systems, 11099 North Torrey Pines, Road, La Jolla, Calif. 92037). The cosmid pCP13 has two ClaI sites, one of which is located in the kanamycin-resistance gene (Darzins et al., *J. Bacteriol.* 59: 9–18 (1984)). The plasmid pUC-Kam is a pUC19 derivative in which the kanamycin resistance gene on a PstI fragment from pUC4K (Vieira et al., *Gene* 19: 259–268 (1982)) was inserted into the ScaI site of pUC19 (James Hartley, Life Technologies, Inc.).

EXAMPLE 3

DNA Isolation

Small scale plasmid DNA isolations were performed by an alkaline lysis method (Maniatis et al., *Molecular Cloning: A Laboratory Manual*, Cold Spring Harbor Laboratory, Cold Spring Harbor, N.Y. (1982)). For large scale preparations, alkaline lysis was followed by a standard CsCl (cesium chloride)-ethidium bromide (EtdBr) gradient centrifugation.

*C. latum* total genomic DNA was isolated by resuspending 2 grams of frozen *C. latum* cells in 8 ml of TNE buffer (50 mM Tris-HCl, pH 8.0, 50 mM NaCl, and 10 mM EDTA). A 10 mg/ml lysozyme solution in TNE buffer was added to the cell suspension to a final concentration of 1 mg/ml. After a 1 hr incubation at 37° C., 10% sodium dodecyl sulfate (SDS) was added to a 2% final concentration and the suspension was shaken gently until lysis was complete. After cell lysis, the lysate was extracted once with phenol and twice with phenol:chloroform:isoamyl alcohol (25:24:1). DNA was spooled with a glass rod under two volumes of cold ethanol. The spooled DNA was dissolved in TE (10 mM Tris-HCl, pH 8.0, and 1 mM EDTA) and purified by CsCl-EtdBr gradient centrifugation.

EXAMPLE 4

DNA Sequencing

Plasmids were sequenced by the cycle sequencing method using The Double Stranded DNA Cycle Sequencing System (LTI, cat#8196SA) which is based on the method described in Krishnan, et al., *Nucl. Acids. Res.* 19: 1153 (1991). Plasmid pBSClaIM6 was sequenced using oligonucleotide #1648 (SEQ ID NO: 1; 5′ GATTTTGATGACGAGCGTAATGGCTGG 3′), which corresponds to the sequence of the kanamycin resistance gene in pCP13 immediately upstream from the HindIII site (Oka et al., *J. Mol. Biol.* 147: 217–226 (1981)). The location of the oligonucleotide #1648 DNA sequence in pBSClaIM6 is indicated as segment #1 in FIG. 2. Plasmid pBSClaM4 was sequenced using the M13 forward and reverse primers described in Krishnen et al., supra.

EXAMPLE 5

Colony and Southern Hybridization

Southern hybridizations were performed using biotinylated probe and photo-gene detection using the Photo Gene Nucleic Acid Detection System (LTI). Fragments generated by endonuclease digestion of the appropriate plasmid were separated by agarose gel electrophoresis and isolated from agarose gel slices by the Gene-Clean procedure (Bio101 Inc, P.O. Box 2284, La Jolla, Calif. 92038-2284). Fragments were then labeled with biotin by octamer-primed synthesis in the presence of biotinylated nucleotides using the BioPrime DNA Labeling System (LTI).

Colony Hybridizations were performed using a radioactive probe essentially as described by Maniatis et al., supra, except that a phosphorimager (Molecular Dynamics, Inc., 880 E. Arques Ave., Sunnyvale, Calif. 94086) was used to detect bound radioactivity. The radioactive probe was labeled with [α-$^{32}$P]dCTP in a polymerase chain reaction (PCR) described herein. The 50 μl PCR mixture contained 50 mM KCl, 25 mM Tris (pH 8.3), 5 mM MgCl$_2$, 200 μM dATP, 200 μM dGTP, 50 μM dCTP, 200 μM dTTP, 100 ng pBSClaIM6, 1 μM oligonucleotide #1718 (SEQ ID NO: 2; 5′ TCACAAATTTTGACTTTTACAAAC 3′), 1 μM oligonucleotide #1719 (SEQ ID NO: 3; 5′ TCCTGAATTTTGGTACTCTACTG 3′), 5 μCi [α-$^{32}$P]dCTP, and 1 unit of Taq DNA polymerase (Perkin Elmer Cetus, 761 Main Ave., Norwalk, Conn. 06859) in water. The 0.6 ml PCR tube was placed in a Techne thermal cycler (LTI) and subjected to the following regimen: 5 min at 94°; 30 cycles of 15 sec at 94°; 15 sec at 55°; 15 sec at 72°; and 2 min at 72°.

The locations of the DNA sequences corresponding to oligonucleotides #1718 and #1719 in pBSClaIM6 are indicated as segments #2 and #3, respectively, in FIG. 2.

EXAMPLE 6

Construction of Genomic Libraries

A cosmid library of *C. latum* genomic DNA was constructed in pCP13. Plasmid pCP13 DNA was digested with an enzyme indicated in Table 1 and dephosphorylated using calf intestine alkaline phosphatase (Boehringer Mannheim). Genomic DNA of *C. latum* was partially digested with the enzyme indicated in the Table 1. One μg of cosmid vector DNA was ligated with 6 μg of the appropriate chromosomal DNA using 2 units of T4 DNA ligase in 1×ligase buffer (LTI) overnight at room temperature. One fourth of the ligated DNA was packaged using LTI's Lambda Packaging System and transfected into DH10B. Approximately $10^4$ tetracycline resistant ($Tc^R$) colonies were pooled and an aliquot was inoculated into 500 ml of Circlegrow media (Bio101) containing tetracycline. After a 5 hour growth at 30°, the cells were harvested and plasmid DNA was purified according to Example 3.

TABLE 1

| Libraries of *C. latum* DNA in cosmid pCP13 and pBluescript | | | |
|---|---|---|---|
| Library | Insertion site in vector | Partial digestion of *C. latum* genomic DNA | ClaI methylase clones obtained |
| PstI | pCP13 PstI | PstI | none |
| SalI | pCP13 SalI | SalI | none |
| HindIII | pCP13 HindIII | HindIII | pCPClaIM1 |
| Sau3AI | pCP13 BamHI | Sau3AI | pCPClaIM8 |
| SphI | pUS-Kam SphI | SphI | none |

For example, the SphI library was constructed by completely digesting *C. latum* genomic DNA with SphI, isolating 8–16 kb DNA fragments using agarose gel electrophoresis, and inserting the DNA fragments into the dephosphorylated SphI site of pUC-Kam. About $10^4$ colonies were pooled, and inoculated into 500 ml of Circlegrow medium containing kanamycin. After 8 hours of growth at 30° C., the cells were harvested and plasmid DNA was prepared as described.

EXAMPLE 7

Selection of Clones Expressing ClaI Methylase

Procedure for selection of ClaI Methylase Clones

Since the selection for ClaI methylase is dependent upon methylation of the ClaI restriction sites, plasmid libraries of *C. latum* DNA in pCP13 (FIG. 1) were subjected to ClaI digestion to eliminate the background of clones lacking the gene for ClaI methylase ("ClaI selection procedure"). In the ClaI selection procedure, 3–5 μg of genomic DNA were digested overnight with 120 units of ClaI. The digested DNA was dephosphorylated, extracted with phenol:chloroform followed by sec-butanol, and precipitated with ethanol.

One-tenth of the digested DNA was used to transform *E. coli* DH10B electrocompetent cells. Plasmid DNA samples isolated from clones selected on plates containing tetracycline or ampicillin were tested for resistance to ClaI. Protection of the resident plasmid and the host chromosomal DNA from digestion with ClaI indicated the presence of methylase activity.

A potential problem in the use of the ClaI selection procedure is that loss of ClaI sites in the vector due to deletions increases the background of clones not containing the ClaI methylase. The SphI library in pUC-Kam did not yield clones which expressed ClaI methylase, but many clones contained vector DNA in which the ClaI site had been deleted. Similarly, the SalI and PstI libraries in pCP13 did not yield ClaI methylase clones, while many of the surviving colonies contained plasmids which were about the size of the cloning vector pCP13 but lacked ClaI sites.

Identification of Methylase Clones

The pCP13 HindIII library was subjected to the ClaI selection procedure and plasmid DNA was isolated from $Tc^R$ clones. All 24 clones tested were identical, and expressed methylase activity as determined by resistance to ClaI restriction digestion of the host DNA. These clones also exhibited endonuclease activity. One clone (pCPClaIM1) was chosen for further study. Of 24 clones which survived the ClaI selection from the pCP13 Sau3AI library, two expressed methylase activity and one was chosen for further study (pCPClaIM8).

Subcloning of the ClaI Methylase Gene

A deletion derivative of the cosmid pCPClaIM1 was generated by digesting pCPClaIM1 with BamHI in order to remove a 6.5 kb BamHI fragment. The BamHI fragment was remote from the part of pCPClaIM1 shown in FIG. 2. After circularizing the modified plasmid (designated "pCPClaMB1") with DNA ligase, plasmid DNA was introduced into DH10B cells.

Partial digestion of pCPClaMB1 with Sau3AI produced 2–4 kb fragments which were subcloned into the BamHI site of pBluescript KS. The library thus formed was selected for resistance to ClaI, and several ClaI methylase subclones were obtained, including pBSClaIM4 and pBSClaIM6.

Restriction mapping indicated that the *C. latum* DNA inserts in pBSClaIM4 and pBSClaIM6 correspond to the *C. latum* DNA insert near one of the two HindIII junctions with pCP13 (FIG. 2). The 2 kb overlap between the two cloned regions closely defined the location of the ClaI methylase gene, which was estimated to be between 0.8 and 1.5 kb in length. Further inspection revealed that pBSClaIM6, but not pBSClaIM4, contained the HindIII junction between *C. latum* DNA and pCP13. Thus, a DNA probe was constructed from this segment of pBSClaIM6 which may be used to detect pCP13 clones containing DNA sequences contiguous with the methylase gene and the probe would not cross-hybridize with pBSClaIM4. As discussed below, this discovery made it possible to design a novel recombinant host which harbored the pBSClaIM4 plasmid and produced the protecting enzyme activity of ClaI methylase. The DNA probe was constructed and designated probe "A" (FIG. 2).

Chromosomal Localization the ClaI Methylase Gene

The *C. latum* genome contiguous to the ClaI methylase gene was mapped to identify which regions were present or missing in the cosmid clones pCPClaIM1, pCPClaIM2 and pCPClaIM3. A restriction map of the *C. latum* chromosome in the region of the ClaI methylase gene was determined using Southern blot analysis of *C. latum* chromosomal DNA digested with various restriction enzymes (FIG. 2). Not one of the three ClaI methylase clones contained a DNA insert representing an intact segment of that region of the chromosome. Failure to clone this region of DNA intact suggested the presence of a functional gene for ClaI endonuclease and/or other lethal gene(s). If the endonuclease gene was present, it was reasonable to assume that previous attempts to clone both genes on a common fragment resulted in the isolation of deletions or other rearrangements which removed the endonuclease gene.

To establish a plasmid expressing both restriction and modification genes in an *E. coli* host, methylation of the host DNA must precede endonuclease digestion. Evidently, the ClaI restriction-modification system cloned in *E. coli* did not exhibit this coordinated expression. Thus, it was hypothesized that utilization of a host already protected with the ClaI methylase would be required to circumvent this problem.

EXAMPLE 8

Selection of Clones Expressing ClaI Endonuclease

Selection of ClaI endonuclease clones required the use of a protected host expressing ClaI methylase. A cosmid library of *C. latum* genomic DNA was constructed in pCP13 using *C. latum* DNA partially digested with Sau3AI. The pCP13 cosmid library packaging mix was introduced into DH10B/pBSClaIM4 (i.e., DH10B cells containing the pBSClaIM4 plasmid).

The 2000 $Ap^R Tc^R$ transformants obtained were subjected to colony hybridization using probe A derived from the *C. latum* DNA which was unique to pBSClaIM6 (FIG. 2). As discussed above, this probe has no homology to pBSClaIM4, but was localized to the region of interest. Therefore, it was used to identify cosmid clones with large chromosomal inserts that might contain the endonuclease gene.

Plasmid DNA samples from colonies which hybridized to probe A were tested for the ability to produce a PCR signal from oligonucleotides #1 and #2. Two out of eleven cultures did so, and these were tested for ClaI endonuclease activity. Both clones exhibited ClaI restriction endonuclease activity. The cosmid isolated from the strain containing the ClaI restriction and methylase genes was designated, pCPClaI402B.

EXAMPLE 9

Assay for Restriction Enzyme

Overnight cultures (20 ml) were harvested and resuspended in 1 ml buffer containing 10 mM Tris-HCl (pH 7.5), 10 mM β-mercaptoethanol and 1 mM EDTA. Cells were sonicated on ice 3 times with 10 second bursts with a micro-tip probe. Lambda DNA substrate (1.0 μg) was digested in 1×REact TM 1 buffer (LTI) with serial dilutions of cell extract for 1 hour at 37° C. DNA was fractionated by electrophoresis and visualized by EtdBr staining. Activity was determined by the presence of the appropriate size bands associated with a ClaI digestion of lambda DNA.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following Claims.

All publications and patent applications mentioned in this specification are indicative of the level of skill of those in the art to which the invention pertains. All publications and patent applications are herein incorporated by reference to the same extent as if each individual publication or patent application was specifically and individually indicated to be incorporated by reference in their entirety.

---

What is claimed is:

1. A recombinant host cell comprising a Caryophanon gene coding for a restriction endonuclease, said restriction endonuclease is capable of recognizing the palindromic sequence:

5'AT ↓ CG AT3'

3'TA GC ↑ TA5' and cleaving said sequence between the deoxythymidine and deoxycytidine residues, producing a two-base 5' extension.

2. The host cell of claim 1, wherein said gene is obtained from *Caryophanon latum*.

3. The host cell of claim 2, wherein said gene is obtained from *Caryophanon latum* BRL 240.

4. The host cell of claim 1, wherein said gene codes for ClaI.

5. A host cell of any one of claims 1 to 4, wherein said host cell is *E. coli*.

6. A vector comprising a Caryophanon gene coding for a restriction endonuclease, said restriction endonuclease is capable of recognizing the palindromic sequence:

5'AT ↓ CG AT3'

3'TA GC ↑ TA5' and cleaving said sequence between the deoxythymidine and deoxycytidine residues, producing a two-base 5' extension.

7. The vector of claim 6, wherein said Caryophanon gene codes for ClaI.

8. The vector of any one of claims 6 or 7, wherein said endonuclease gene is under control of a ClaI endonuclease gene promoter.

9. The vector of any one of claims 6 or 7, wherein said endonuclease gene is under control of an inducible promoter.

10. The vector of claim 9, wherein said promoter is lambda $P_L$ promoter.

11. The vector of claim 9, wherein said promoter is a tac promoter.

12. A method of producing a restriction endonuclease which recognizes the palindromic sequence:

5'AT ↓ CG AT3'

3'TA GC ↑ TA5' and cleaves said sequence between the deoxythymidine and deoxycytidine residues, producing a two-base 5' extension, said method comprising:

(a) culturing a recombinant host cell comprising a Caryophanon gene coding for said restriction endonuclease; and (b) isolating said restriction endonuclease from said host cell.

13. The method of claim 12, wherein said gene is obtained from *Caryophanon latum*.

14. The method of claim 13, wherein said gene is obtained from *Caryophanon latum* BRL 240.

15. The method of claim 12, wherein said gene codes for ClaI.

16. The method of any one of claims 12 to 15, wherein said host cell is *E. coli*.

17. The method of any one of claims 12 to 15, wherein said gene is contained in a vector.

18. The method of any one of claims 12 to 15, wherein said endonuclease gene is under control of a ClaI endonuclease gene promoter.

19. The method of any one of claims 12 to 15, wherein said gene is under control of an inducible promoter.

20. The method of claim 19, wherein said promoter is a lambda $P_L$ promoter.

21. The method of claim 19, wherein said promoter is a tac promoter.

22. A method of using the vector of any one of claims 6 to 11, to prepare a restriction endonuclease, said method comprising:

(a) introducing said vector into a host cell to produce a recombinant host cell;

(b) culturing said recombinant host cell; and (c) isolating said restriction endonuclease from said recombinant host cell.

23. A recombinant host cell comprising a Caryophanon gene coding for a modification methylase, said modification methylase is capable of recognizing the palindromic sequence:

5'ATCGAT3'

3'TAGCTA5' and chemically modifying said sequence such that said modified sequence is resistant to cleavage with its corresponding restriction endonuclease.

24. The host cell of claim 23, wherein said gene is obtained from *Caryophanon latum*.

25. The host cell of claim 24, wherein said gene is obtained from *Caryophanon latum* BRL 240.

26. The host cell of claim 23, wherein said gene codes for ClaI modification methylase.

27. A host cell of any one of claims 23 to 26, wherein said host cell is *E. coli*.

28. A vector comprising a Caryophanon gene coding for a modification methylase, said modification methylase is capable of recognizing the palindromic sequence:

5'ATCGAT3'

3'TAGCTA5' and chemically modifying said sequence such that said modified sequence is resistant to cleavage with its corresponding restriction endonuclease.

29. The vector of claim 28, wherein said Caryophanon gene codes for ClaI modification methylase.

30. The vector of any one of claims 28 or 29, wherein said modification methylase gene is under control of a ClaI modification methylase gene promoter.

31. The vector of any one of claims 28 or 29, wherein said modification methylase gene is under control of an inducible promoter.

32. The vector of claim 31, wherein said promoter is lambda $P_L$ promoter.

33. The vector of claim 31, wherein said promoter is a tac promoter.

34. A method of producing a modification methylase which recognizes the palindromic sequence:

5'ATCGAT3'

3'TAGCTA5' and modifies said sequence such that said modified sequence is resistant to cleavage with its corresponding restriction endonuclease, said method comprising:
  (a) culturing a recombinant host cell comprising a Caryophanon gene coding for said modification methylase; and
  (b) isolating said modification methylase from said host cell.

35. The method of claim 34, wherein said gene is obtained from *Caryophanon latum*.

36. The method of claim 35, wherein said gene is obtained from *Caryophanon latum* BRL 240.

37. The method of claim 34, wherein said gene codes for ClaI modification methylase.

38. The method of any one of claims 34 to 37, wherein said host cell is *E. coli*.

39. The method of any one of claims 34 to 37, wherein said gene is contained in a vector.

40. The method of any one of claims 34 to 37, wherein said modification methylase gene is under control of a ClaI modification methylase gene promoter.

41. The method of any one of claims 34 to 37, wherein said modification methylase gene is under control of an inducible promoter.

42. The method of claim 41, wherein said promoter is a lambda $P_L$ promoter.

43. The method of claim 41, wherein said promoter is a tac promoter.

44. A method of using the vector of any one of claims 28 to 33, to prepare a modification methylase, said method comprising:
  (a) introducing said vector into a host cell to produce a recombinant host cell;
  (b) culturing said recombinant host cell; and
  (c) isolating said modification methylase from said recombinant host cell.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: both
        ( D ) TOPOLOGY: both ( x i ) SEQUENCE DESCRIPTION: SEQ ID NO:1:

```
GATTTTGATG ACGAGCGTAA TGGCTGG                                    27
```

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: both
        ( D ) TOPOLOGY: both ( x i ) SEQUENCE DESCRIPTION: SEQ ID NO:2:

```
TCACAAATTT TGACTTTTAC AAAC                                       24
```

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: both
        ( D ) TOPOLOGY: both ( x i ) SEQUENCE DESCRIPTION: SEQ ID NO:3:

```
TCCTGAATTT TGGTACTCTA CTG                                                    2 3
```